United States Patent
Inukai et al.

(10) Patent No.: US 7,279,590 B2
(45) Date of Patent: Oct. 9, 2007

(54) PREPARATION OF ORGANOHALOSILANES

(75) Inventors: Tetsuya Inukai, Annaka (JP); Hajime Ishizaka, Annaka (JP); Mikio Aramata, Annaka (JP); Yukinori Satou, Annaka (JP)

(73) Assignee: Shin-Estu Chemical Co., Ltd., Tokyo (JP)

( * ) Notice: Subject to any disclaimer, the term of this patent is extended or adjusted under 35 U.S.C. 154(b) by 1 day.

(21) Appl. No.: 11/081,561

(22) Filed: Mar. 17, 2005

(65) Prior Publication Data

US 2005/0209474 A1 Sep. 22, 2005

(30) Foreign Application Priority Data

Mar. 18, 2004 (JP) ............................. 2004-077709

(51) Int. Cl.
*C07C 7/04* (2006.01)
(52) U.S. Cl. ........................................................ 556/472
(58) Field of Classification Search ................. 556/472
See application file for complete search history.

(56) References Cited

U.S. PATENT DOCUMENTS

| | | | |
|---|---|---|---|
| 2,380,995 A | 8/1945 | Rochow et al. | |
| 4,500,724 A | 2/1985 | Ward, III et al. | |
| 4,602,101 A | 7/1986 | Halm et al. | |
| 5,059,706 A | 10/1991 | Degen et al. | |
| 5,622,682 A * | 4/1997 | Tom | 423/230 |
| 6,005,130 A | 12/1999 | Lewis et al. | |
| 6,025,513 A * | 2/2000 | Nakanishi et al. | 556/472 |
| 6,215,012 B1 * | 4/2001 | Ueno et al. | 556/472 |
| 6,218,562 B1 * | 4/2001 | Aramata et al. | 556/472 |
| 6,242,629 B1 * | 6/2001 | Ueno et al. | 556/472 |
| 6,288,258 B1 | 9/2001 | Aramata et al. | |
| 6,365,766 B1 | 4/2002 | Aramata et al. | |
| 6,395,917 B1 * | 5/2002 | Ishizaka et al. | 556/472 |
| 6,506,923 B2 | 1/2003 | Inukai et al. | |
| 6,686,312 B1 | 2/2004 | Aramata et al. | |

FOREIGN PATENT DOCUMENTS

| | | |
|---|---|---|
| JP | 5-51596 B2 | 8/1993 |
| JP | 6-92421 A | 11/1994 |
| JP | 2000-176296 A | 6/2000 |
| JP | 2000-254506 A | 9/2000 |
| JP | 2000-296334 A | 10/2000 |

(Continued)

OTHER PUBLICATIONS

Frank Komitsky et al., Silicon for the Chemical Industry IV, Geiranger, Norway (1998) pp. 217-225.

(Continued)

*Primary Examiner*—Johann Richter
*Assistant Examiner*—Chukwuma Nwaonicha
(74) *Attorney, Agent, or Firm*—Birch, Stewart, Kolasch & Birch, LLP

(57) ABSTRACT

Organohalosilanes are prepared by reacting metallic silicon particles with an organohalide in the presence of a copper catalyst. A contact mass composed of metallic silicon and copper catalyst contains an effective amount of a catalyst powder obtained by mechanical surface treatment of a powder mixture of tin powder and another metal, typically copper powder, on a ball mill, stamp mill, jet mill, mechanofusion device or the like.

22 Claims, 1 Drawing Sheet

FOREIGN PATENT DOCUMENTS

| | | |
|---|---|---|
| JP | 2001-122880 A | 5/2001 |
| JP | 2002-128786 A | 5/2002 |
| JP | 2002-241384 A | 8/2002 |
| JP | 2003-313191 A | 11/2003 |
| RU | 122749 A | 1/1959 |
| RU | 178817 A | 3/1966 |
| RU | 237892 A | 11/1969 |

OTHER PUBLICATIONS

L. Rosch, W. Kalchauer et al., Silicon for the Chemical Industry IV, Sandefjord, Norway (1996), pp. 269-273.

* cited by examiner

PREPARATION OF ORGANOHALOSILANES

CROSS-REFERENCE TO RELATED APPLICATION

This non-provisional application claims priority under 35 U.S.C. §119(a) on Patent Application No. 2004-077709 filed in Japan on Mar. 18, 2004, the entire contents of which are hereby incorporated by reference.

This invention relates to an industrial process for preparing organohalosilanes.

BACKGROUND OF THE INVENTION

With respect to the synthesis of alkylhalosilanes, Rochow first disclosed in U.S. Pat. No. 2,380,995 direct synthesis reaction between metallic silicon and alkyl halide in the presence of a copper catalyst. Since then, there have been reported a number of research works relating to various co-catalysts used together with copper catalysts, reactors, additives used during reaction, and the like. In the industrial synthesis of organohalosilanes, the selectivity of diorganodihalosilane which is most widely used in silicone resins, the formation rate of silanes, and the percent conversion of metallic silicon into useful silane are crucial. The selectivity of diorganodihalosilane is evaluated in terms of a weight or molar ratio of dialkyldihalosilane to the silane product and a T/D ratio.

Organohalosilane products contain diorganodihalosilane (D), triorganohalosilane (M), organotrihalosilane (T), etc. as well as by-products such as organohydrodihalosilane (H) and organohalodisilane. In particular, disilanes are known as a high-boiling fraction among silicone manufacturers using direct method organohalosilanes because few processes are available for the effective utilization of disilanes, and most disilanes are discarded as residues. The T/D ratio is a compositional ratio of organotrihalosilane to diorganodihalosilane in the entire organohalosilanes produced, with a lower T/D ratio being preferred. The formation rate of organohalosilane is represented by a space time yield (STY) which is the weight of crude organohalosilane produced per unit time relative to the weight of metallic silicon held in the reactor. In order to improve the content of diorganohalosilane produced, reduce the T/D ratio or increase the STY, various research works have been made with a focus on the catalyst and co-catalyst.

USSR Application Specification No. 617,569 (Certificate of inventorship No. 122,749) dated 24 Jan. 1959 discloses reaction in the presence of metallic silicon-copper alloy with 20 to 40 ppm of antimony added. Allegedly, the dimethyldichlorosilane content is improved from 40% to 60%. U.S. Pat. No. 4,500,724 discloses use of a copper/zinc/tin catalyst containing 200 to 3,000 ppm of tin, thereby achieving an improvement of T/D to 0.037. Japanese Patent Publication (JP-B) No. 6-92421 discloses reaction using copper arsenide having an arsenic concentration of at least 50 ppm. It is described in these patent references that reactivity, more specifically the rate of reaction of metallic silicon is improved by adding these tin, antimony and arsenic co-catalysts to a reaction contact mass comprising metallic silicon and copper.

USSR Application Specification No. 903,369 (Certificate of inventorship No. 178,817) dated 2 Jun. 1964 discloses that a co-catalyst selected from the group consisting of zinc, bismuth, phosphorus (200 ppm), arsenic, tin, and iron improves the dimethyldichlorosilane content to 72.1% from the value achieved by the above-referred Application Specification No. 617,569 (Certificate of inventorship No. 122,749). Also USSR Application Specification No. 1,152,943 (Certificate of inventorship No. 237,892) dated 20 Nov. 1969 discloses to add a phosphorus-copper-silicon alloy to a contact mass so as to give 2,500 to 30,000 ppm of phosphorus, thereby improving the dimethyldichlorosilane content to 82.3%. Moreover, U.S. Pat. No. 4,602,101 corresponding to JP-B 5-51596 discloses that 25 to 2,500 ppm of a phosphorus compound capable of generating elemental phosphorus in the reactor is added to a contact mass. Although the results of reaction according to this US patent are improved over the last-mentioned USSR patent, there still remain many problems including hazard imposed by spontaneously igniting elemental phosphorus and increased cost of raw materials. Then this US patent is also unsuitable to apply to commercial scale reactors. Also, F. Komitsky et al., Silicon for the Chemical Industry IV, Geiranger, Norway (1998), page 217, proposes the addition of phosphorus in the form of copper phosphide, leaving problems including a low percent conversion, ineffective utilization of phosphorus, and difficult control of a phosphorus concentration. U.S. Pat. No. 6,025,513 intends to add boron to a contact mass wherein the boron concentration is controlled so as to improve productivity. U.S. Pat. No. 5,059,706 discloses to introduce a phosphorus compound in a vapor phase into a reactor for increasing selectivity. U.S. Pat. No. 6,005,130 discloses to introduce organomonophosphine for increasing selectivity.

However, the phosphorus base additives used in the prior art have an outstanding trade-off between activity and composition selectivity. In particular, it is pointed out that oxide originating from phosphorus can exacerbate flow on the particle surface. Therefore, the conventional phosphorus base additives offer few merits on the continuous operation of commercial scale reactors. Other additives are known from L. Rosch, W. Kalchauer et al., Silicon for the Chemical Industry IV, Sandefjord, Norway (1996) wherein monomethyldichlorosilane is introduced for improving activity. This additive is effective only at the initial period, but not regarded as exerting a lasting effect during the continuous operation of commercial scale reactors.

While most prior art proposals focus on the elements of which the catalyst is made, as found in the foregoing references, some proposals to improve catalysis have recently been made from a brand new point of view. For example, U.S. Pat. No. 6,686,312 (corresponding to JP-A 2000-254506) discloses the use of a thermally active metallic copper powder having a large quantity of strain energy; and U.S. Pat. No. 6,365,766 (corresponding to JP-A 2000-296334) discloses the use of a copper powder in the form of flakes or scales, both for industrially advantageous preparation of organohalosilanes.

Aiming to establish a catalyst system in which both the chemical action and powder properties of a powdered catalyst contribute to improved productivity, U.S. Pat. No. 6,506,923 (corresponding to JP-A 2002-241384) proposes preparation of organohalosilanes using a catalytic metal or alloy powder as atomized.

The inventors proposed in U.S. Pat. No. 6,288,258 (corresponding to JP-A 2001-122880) efficient preparation of organohalosilanes at a reduced T/D ratio of trioganohalosilane to diorganodihalosilane by adding phosphor bronze to the catalyst.

JP-A 2000-176296 discloses a method of preparing a contact mass for organohalosilane synthesis comprising the step of applying high shear forces to metallic silicon particles and metallic copper particles in a non-oxidizing atmosphere for rubbing the particles together, thereby forming a metallic copper thin film on at least part of surfaces of metallic silicon particles. U.S. Pat. No. 6,395,917 (corresponding to JP-A 2002-128786) discloses a process of preparing organohalosilanes in which shear forces are applied to a mixture of catalyst and/or co-catalyst particles and finely divided silica for mutually rubbing the particles, thereby producing the catalyst and/or co-catalyst having finely divided silica attached to surfaces thereof, which is used in the contact mass. Additionally, JP-A 2003-313191 proposes the preparation of organohalosilanes by using a fine dispersion of a cesium-containing compound in a contact mass. None of these methods are fully satisfactory in formation rate, useful silane yield, catalyst longevity, silicon reaction yield or the like.

SUMMARY OF THE INVENTION

An object of the invention is to provide a novel and improved process for preparing organohalosilanes at a drastically increased formation rate.

Continuing research works on the development of co-catalysis, the inventors have made investigations to derive more advantage from tin element that can exert its effect even in an extremely low amount. When metallic tin is used alone as the tin source, due to its melting point of 231.97° C. and its reaction temperature below 250 to 300° C., an excess of metallic tin will collect at the bottom of the reactor during long-term operation, clogging the reactor bottom and exacerbating the flow. When tin oxide is used as the tin source, it gives little contribution to the activation of the contact mass in the initial stage of reaction and is thus deleterious in increasing the production rate from the initial. As to tin-containing alloys, a number of types are known from the past. In most cases, however, practical tin-containing alloys which are known in the art are standardized to have specific tin contents of at least 2% by weight (all percents are by weight, hereinafter, unless otherwise stated). When these alloys are used in preparation of organohalosilanes, tin cumulates to a higher concentration and more disilanes form accordingly, resulting in an activity loss and a failure of long-term service. The inventors then attempted to introduce an optimum amount up to 1% of tin into a catalyst powder. However, it was surprisingly difficult in practice to uniformly introduce an intended amount up to 1% of tin into copper or copper alloy for use as a catalyst powder. It imposes a practical task to the powder metallurgical preparation stage.

It is well known in the metallurgy that copper and tin can be combined in any proportion to form a solid solution. In general, tin bronze has a nominal composition ranging from 2% to 35% tin. In terms of nominal composition, the tin bronze used in the art is divided into the following three groups:

(1) Sn 2-10%; most widespread use with some zinc, iron or the like added. Those alloys with relatively low tin contents are used as artistic bronze in the preparation of medals, coins and objects of arts and crafts. Those alloys with relatively high tin contents of the order of 10% are known as "gun metal" and used as ship and machine components due to excellent strength and corrosion resistance.

(2) Sn 15-20%; used as castings.

(3) Sn ~30%; used as mirrors in the past.

Since bronze used as practical alloy in the prior art has compositions far apart from the alloy containing up to 1% Sn as contemplated herein, the inventors have to originally develop alloys with low Sn concentrations. However, copper alloys with Sn contents of up to 1% were found to be quite difficult to acquire the desired concentration in the alloy preparation stage. It is known that the segregation of tin in the cast state can be solved by annealing. In a case wherein a copper-tin alloy with a Sn content of up to 1% is used as the catalyst powder, for example, since it can be achieved by no means to eliminate or mitigate variations of tin concentration within the ingot at a stage prior to comminution such as by stamping or variations of tin concentration in an alloy powder as atomized, it is difficult to use a copper-tin powder, prepared by way of a solid-solution phase containing up to 1% tin, as a catalyst for precise synthesis of organohalosilanes. Such copper-tin alloys are not effective for use as the catalyst powder, because tin fails to exert its co-catalysis to a sufficient extent. Additionally, when the solid-solution phase comes in contact with the air in the melting stage, tin is oxidized into tin oxide or the like and thus converted to a slug state. For tin contents of the order of 1% or less, the quantity of tin removed from the solid-solution phase is not negligible. This problem might be solved by substituting an inert gas for the ambient gas surrounding the contact surface in the melting stage. This requires large amounts of installation investment and is impractical from the economic aspect.

Then the inventors attempted to form a powder having a uniform distribution of tin throughout by combining a desired trace amount of tin powder with a metal powder, typically copper powder and mechanically treating surfaces of the resulting powder mixture for composite formation. The inventors have found that by employing such a technique as ball milling, stamping or mechanofusion, a catalyst powder having a controlled low concentration of Sn can be produced at a relatively low cost and without a substantial loss of the feed material. Applying such a catalyst powder to the preparation of organohalosilanes, the inventors have succeeded in improving productivity and longevity.

To solve actual issues associated with preparation of the catalyst powder for use in the direct method or Rochow method, the present invention intends to provide a catalyst powder of copper or copper alloy having tin uniformly distributed in a desired concentration of up to 1%. The inventors have found that the use of a catalyst powder obtained through mechanical surface treatment of a powder mixture of a metal powder and a tin powder is simple and cost-effective in the manufacture of catalyst powder and achieves substantial improvements in productivity and longevity in the manufacture of organohalosilanes.

More particularly, a catalyst powder is obtained by mechanical surface treatment of a powder mixture of a metal or alloy powder and a tin powder on a mechanical grinding or mixing device such as a ball mill, stamp mill, vertical roller mill, mechanofusion device, jet mill, attritor or cosmophoresis mixer. With respect to the preparation of organohalosilanes, the inventors have found that the rate of formation of useful silane is increased when a catalyst powder obtained by mechanical surface treatment of a powder mixture of a metal or alloy powder and a tin powder on the above-specified mechanical grinding or mixing device is added to a contact mass composed of metallic silicon and a catalyst component. Under the situation that in designing the function of a catalyst for use in the direct method, a copper alloy containing 1% or less of tin was quite difficult to prepare to the desired concentration in the alloy preparation stage, the inventors attempted to effect mechanical treatment on surfaces of a powder mixture of a metal powder, typically metallic copper powder and a desired trace amount of tin powder for composite formation so that tin is uniformly distributed over the entire powder. To reduce the concept into effect, the inventors selected a mechanical grinding or mixing device from a ball mill, stamp mill, vertical roller mill, mechanofusion device, jet mill, attritor and cosmo-phoresis mixer; effected mechanical or mechano-chemical treatment on surfaces of a powder mixture of a metal or alloy powder and a tin powder on the selected grinding or mixing device to produce a catalyst powder; and applied the resulting catalyst powder to the direct method.

The use of the catalyst powder obtained by mechanical surface treatment of a powder mixture of a metal powder and a tin powder provides for a process of improving the rate of formation of useful silane and its longevity by employing a mechanical treatment which is simple and inexpensive to prepare a copper alloy containing 1% or less of tin, and forming a contact mass containing an effective amount of a catalyst powder obtained by the mechanical mixing or grinding technique. Based on this concept, the inventors studied a series of catalytic metal powders and attempted to synthesize organohalosilanes by reacting metallic silicon with an organohalide in the presence of metallic copper or a copper compound catalyst such as copper chloride, copper oxide or copper acetate and optionally, a co-catalyst like metallic zinc, zinc-copper alloys or zinc compounds such as zinc chloride, zinc oxide or zinc acetate; metallic tin, lead-copper alloys or tin compounds such as tin chloride or tin oxide; metallic antimony or antimony compounds such as antimony chloride or antimony oxide; metallic aluminum or aluminum compounds such as aluminum chloride or aluminum oxide; metallic phosphor, inorganic phosphorus compounds such as phosphorus trichloride or phosphorus oxide, monoalkylphosphines such as trimethylphosphine or triphenylphosphine, or polyorganophosphine compounds such as organic diphosphines. The inventors have discovered that the use of a contact mass containing an effective amount of a catalyst powder obtained by mechanical surface treatment of a powder mixture of a tin powder and a metal powder other than tin is effective in improving the rate of formation of organohalosilanes and increasing the yield of silicon reaction without reducing the proportion of useful silane. It is emphasized that the use of a contact mass containing an effective amount of a catalyst powder obtained by mechanical surface treatment of a powder mixture of a tin powder and a metal powder other than tin is successful in achieving a markedly increased rate of formation of organohalosilanes without a substantial change in the useful silane content.

The present invention provides a process for preparing organohalosilanes having the general formula (I):

$$R_k(H)_m SiX_{(4-k-m)}$$

wherein R is a monovalent hydrocarbon group of 1 to 12 carbon atoms, X is a halogen atom, k is an integer of 1 to 3, m is an integer of 0 to 2, and the sum of k+m is 1 to 3, by reacting metallic silicon particles with an organohalide in the presence of a copper-containing catalyst. A contact mass composed of the metallic silicon and a copper-containing catalyst component contains an effective amount of a catalyst powder which is obtained by mechanical surface treatment of a powder mixture of a tin powder and a metal powder other than tin.

The mechanical surface treatment is typically carried out on a mechanical grinding or mixing device selected from among a ball mill, stamp mill, vertical roller mill, mechanofusion device, jet mill, attritor, and cosmo-phoresis mixer.

In preferred embodiments, the catalyst powder is obtained by mechanical surface treatment of a powder mixture of a tin powder and a copper or copper alloy powder; the catalyst powder typically contains up to 1% by weight of tin; and the catalyst powder has a bulk specific gravity of 0.3 to 5 g/cm$^3$ and an average particle size of 1 to 200 µm as measured by laser diffraction particle size distribution analysis.

Also preferably, the catalyst component comprises metallic copper or a copper compound and optionally a co-catalyst selected from the group consisting of metallic zinc, zinc compounds, metallic tin, tin compounds, metallic antimony, antimony compounds, metallic aluminum, aluminum compounds, metallic phosphorus and phosphorus compounds.

In the preparation of organohalosilanes, the use of a contact mass containing an effective amount of a catalyst powder obtained by mechanical surface treatment of a powder mixture of a tin powder and a metal powder is successful in achieving a markedly increased rate of formation of organohalosilanes, its longevity, and an increased utilization of silicon without a lowering in selectivity of useful silane.

BRIEF DESCRIPTION OF THE DRAWINGS

The only FIGURE, FIG. 1 schematically illustrates a mechanofusion device.

DESCRIPTION OF THE PREFERRED EMBODIMENTS

Figure 1:
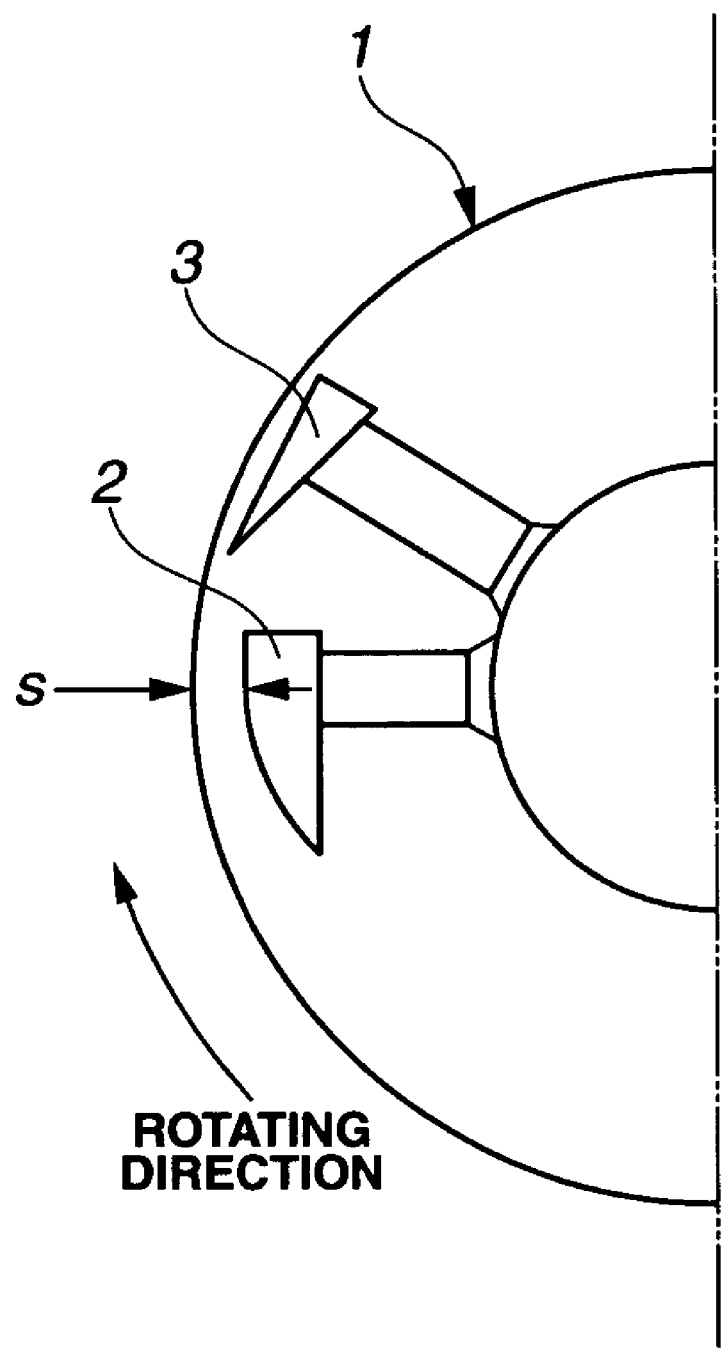

The process for preparing organohalosilanes according to the invention involves the step of reacting metallic silicon particles with an organohalide in the presence of a copper-containing catalyst to thereby form organohalosilanes of the following general formula (I):

$$R_k(H)_m SiX_{(4-k-m)} \qquad (I)$$

wherein R is a monovalent $C_1$-$C_{12}$ hydrocarbon group, X is a halogen atom, k is an integer of 1 to 3, m is an integer of 0 to 2, and k+m is an integer of 1 to 3.

The process of the invention can be carried out in any of fixed bed reactors, stirred bed reactors and fluidized bed reactors. From the industrial aspect, a fluidized bed reactor suited for continuous operation is advantageously employed.

The metallic silicon used herein preferably has a silicon purity of at least 97% by weight, especially at least 98% by weight. Prior to use, the metallic silicon is preferably ground into particles with an appropriate particle size. Where the reactor used is a fluidized bed or stirred bed reactor, the metallic silicon powder should preferably have a particle size in the range of 5 to 150 µm, corresponding to 50% of the weight base cumulative size distribution curve on sieving, in order that the metallic silicon powder have good fluidity.

The organohalides to be reacted with metallic silicon to form organohalosilanes are preferably of the following general formula (II):

$$RX \qquad (II)$$

wherein R is a monovalent hydrocarbon group of 1 to 12 carbon atoms, preferably 1 to 6 carbon atoms. Examples of R include aryl groups such as phenyl and tolyl, aralkyl groups such as benzyl, phenylethyl and phenylpropyl, alkenyl groups such as vinyl, allyl, propenyl and butenyl, and alkyl groups such as methyl, ethyl, propyl, butyl and hexyl, with methyl and phenyl being most preferred. X is a halogen atom, typically chlorine or bromine. Illustrative of suitable organohalides are methyl chloride, ethyl chloride, propyl chloride, methyl bromide, ethyl bromide, benzene chloride and benzene bromide. Of these, methyl chloride and benzene chloride are preferable in the industry. Methyl chloride is most useful because dimethyldichlorosilane produced therefrom finds a wide variety of applications as the raw material for many silicone resins. The organohalide is previously heated and gasified before it is fed into the reactor. The organohalide gas may be fed alone or along with an inert gas in a sufficient amount to fluidize the contact mass. The fluidizing amount is determined as appropriate from the diameter of the reactor and the superficial velocity.

In the reaction of metallic silicon with organohalosilanes, there is added a copper-containing catalyst, simply referred to as copper catalyst. The copper catalyst may be selected from various forms of copper including elemental copper (or metallic copper) such as powdered copper and stamped copper, and copper compounds such as cuprous oxide, cupric oxide, copper halides (e.g., copper chloride) and copper acetate. Any of promoters such as zinc, tin, antimony, and arsenic may be used as the co-catalyst. The co-catalyst may be used alone or in the form of an alloy with copper. Suitable combinations of the copper catalyst with the co-catalyst are copper alloys including Cu-Zn, Cu-Sn, and Cu-Zn-Sn (or Sb or As). Examples of the other co-catalyst include metallic zinc, zinc compounds such as zinc chloride, zinc oxide, and zinc acetate, metallic tin, tin compounds such as tin chloride and tin oxide, metallic antimony, antimony compounds such as antimony chloride and antimony oxide, metallic aluminum, aluminum compounds such as aluminum chloride and aluminum oxide, metallic phosphorus, inorganic phosphorus compounds such as phosphorus trichloride and phosphorus oxide, monoalkylphosphines such as trimethylphosphine and triphenylphosphine, and polyorganophosphine compounds such as organic diphosphine compounds. Any of these copper catalysts may be admitted alone into the reactor.

An appropriate amount of the copper catalyst charged is about 0.1 to 10 parts, and more preferably about 2 to 8 parts by weight, calculated as copper, per 100 parts by weight of the metallic silicon powder. Also the co-catalyst is used in an effective amount which is determined depending on its identity. Specifically, zinc is used in an amount of 0.05 to 1 part by weight per 100 parts by weight of the metallic silicon powder; tin, antimony or arsenic, alone or in combination, is used in a (total) amount of 0.001 to 0.05 part, especially 0.005 to 0.01 part by weight per 100 parts by weight of the metallic silicon powder.

According to the invention, an effective amount of a catalyst powder obtained by mechanical surface treatment of a powder mixture of a tin powder and a metal powder other than tin is added to a contact mass composed of the above-described metallic silicon and the copper-containing catalyst component before reaction between metallic silicon and an organohalide is carried out.

When a catalyst powder is obtained by mechanical surface treatment of a powder mixture of a tin powder and a metal powder other than tin, the preferred source for the catalyst powder is a copper powder, brass powder, bronze powder, or a catalytic alloy powder containing two or more elements selected from among copper, zinc, tin, phosphorus, nickel, cobalt, iron, manganese, chromium, tungsten, molybdenum, boron, silicon and carbon. Of these, the more preferred metal powder other than tin is a copper powder or an alloy powder of copper with an element or elements other than tin (as mentioned above). The copper alloy powder should preferably have a copper content of at least 99%, most preferably at least 99.25%. The catalyst powder should preferably have a tin content of up to 1%, more preferably up to 0.75%. The lower limit of the tin content is preferably at least 0.001%, more preferably at least 0.01%.

When a catalyst powder is prepared by mechanical surface treatment of a powder mixture of a tin powder and a metal powder other than tin, the mechanical treatment should apply high shear forces to particles for inducing rubbing or collision of particles together, thereby mechanically treating surfaces of tin particles and metal particles in admixture, so that fine particles may attach to surfaces of coarse particles or particles mechanically join together to create a new chemical bond state on the mass surface, achieving the desired effects of the invention. For example, tin particles attach to some or entire surfaces of metal particles. Alternatively, metal particles have a multilayer cover formed on their surfaces in which surfaces of metal cores are coated with a tin layer, then with a metal layer, and further with another tin layer. Effective mechanical surface treatment may be carried out using any device that can provide particles with such a surface state. A mechanical grinding or mixing device used for this purpose is typically selected from among a ball mill, stamp mill, vertical roller mill, mechanofusion device, jet mill, attritor, and cosmophoresis mixer. Therefore, the term "surface treatment" as used herein means that surfaces of tin particles and metal particles undergo high shear forces on the above grinding or mixing device so that particles of one type are attached to particles of the other type. Of the above-mentioned devices, the mechanofusion device is most preferred.

Referring to FIG. 1, a mechanofusion device (AM-15F) is schematically illustrated. The device includes a rotating casing 1 and a stationary support having inner pieces 2 and scrapers 3 mounted thereon (only one set of an inner piece and a scraper is shown). The scraper 3 is located downstream of the inner piece 2 with respect to the rotating direction of the casing 1. Raw materials (tin particles and metal particles) are admitted into the casing 1. The casing 1 is rotated to centrifugally push the raw materials against the inner wall of the casing 1 and shear forces are applied to the raw materials between the inner piece 2 and the casing 1 whereby particles are intimately dispersed. The raw materials modified between the casing 1 inner wall and the inner piece 2 is scraped off by the scraper 3. In this way, the operation of applying shear forces to the raw materials is repeated. It is noted that the casing 1 is cooled in order to avoid any abnormal temperature rise by frictional heat. Namely, the mechanofusion device has the rotating casing 1 and the stationary inner piece 2 which cooperate to apply compression, shear and grinding actions to powder particles. The scraper 3 serves to scrape off the powder compressed between the inner piece 2 and the casing 1. The device is capable of applying mechanical energy to particles of plural materials to achieve (1) surface fusion, (2) dispersion and mixing, and (3) particle size control.

It is understood that actual operation is carried out by monitoring the power to the motor and the temperature of the powder particles at the inner piece.

The number of revolutions of the casing 1 and the clearance S between the casing 1 and the inner piece 2 are properly selected depending on a particular type of device used. It is preferred for the AM-15F mechanofusion device that the casing 1 be rotated at 300 to 3,000 rpm, and especially 800 to 2,200 rpm, and the clearance be set at 0.1 to 10 mm, and especially 0.5 to 5 mm.

The surface treatment should preferably be carried out in a non-oxidizing atmosphere, such as nitrogen gas, argon gas, hydrogen gas or a mixture thereof.

The catalyst powder obtained through the mechanical surface treatment should preferably have a specific surface area of about 0.01 to 0.5 m²/g, and especially about 0.025 to 0.35 m²/g as measured by the BET or air permeability method. Reactivity gives preference to an average particle size in the range of 1 to 200 µm, more preferably 2 to 100 µm, and most preferably 5 to 75 µm, as measured by laser diffraction particle size distribution analysis. Further, fluidity gives preference to a bulk specific gravity of 0.3 to 5 g/cm³, more preferably 0.4 to 4 g/cm³.

To improve the productivity of organohalosilanes, the catalyst powder obtained through mechanical surface treatment of a powder mixture of a tin powder and a metal powder is desirably used in an effective amount relative to the total amount of silicon and depending on the reaction time, scale and metallic silicon grade. The effective amount is preferably 0.01 to 5%, more preferably 0.05 to 3% based on the contact mass.

In the step of heating the contact mass or imparting catalytic activity to the contact mass, an inert gas is used for fluidizing the contact mass in the reactor. Such an inert gas may be nitrogen or argon gas, for example, with the nitrogen gas being preferable from the economic standpoint. The flow velocity of the inert gas fed in this and subsequent steps is at least the minimum fluidization velocity of the contact mass, and preferably about 5 times the minimum fluidization velocity. A flow velocity below the range of the inert gas may often fail to achieve uniform fluidization of the contact mass. If the flow velocity of the inert gas is above the range, metallic silicon powder may be excessively scattered with increased losses of the inert gas and heat. It is recommended to recycle the inert gas.

After the contact mass is heated to the reaction temperature or given catalytic activity as mentioned above, the organohalide is introduced into the reactor where gas-solid catalytic reaction takes place between the organohalide and silicon to form organohalosilanes. The conditions for this gas-solid catalytic reaction may be as in the conventional Rochow method. For example, the reaction is preferably effected at a temperature of about 250 to 600° C., and especially about 350 to 500° C.

The above reaction forms organohalosilanes of the general formula (I):

$$R_k(H)_m SiX_{(4-k-m)} \quad (I)$$

wherein R is a monovalent $C_1$-$C_{12}$ hydrocarbon group, X is a halogen atom, k is an integer of 1 to 3, m is an integer of 0 to 2, preferably 0 or 1, and k+m is an integer of 1 to 3. It is preferred from the demand balance that m be approximately zero and k be approximately 1 to 2, both on the average. Then there is obtained a product containing a larger proportion, typically 50 to 95%, of diorganodihalosilane (D) wherein k=2 and m=0 which is most useful as the source to silicones and a less proportion of organotrihalosilane (T) wherein m=0. In ideal reaction conditions that avoid contact with Lewis acid such as ferric chloride, for example, a T/D ratio of typically 0.3 or less, and especially 0.1 or less is achievable.

EXAMPLE

Examples of the invention are given below by way of illustration and not by way of limitation. All parts and percents are by weight unless otherwise stated. The average particle size was measured by a particle size distribution analyzer based on the laser diffraction method (Shimadzu Mfg. Co., Ltd.). The bulk specific gravity was measured by a powder tester (Hosokawa Micron Co., Ltd.). An average value of the cumulative content of useful silane was determined by a gas chromatograph (Hitachi Ltd.).

Example 1

A fluidized bed reactor of carbon steel having a diameter of 75 mm and a height of 900 mm was charged with 100 parts of metallic silicon powder, a catalyst mixture of 4 parts metallic copper powder, 0.2 part zinc and 0.1 part tin, and 0.5 part of a catalyst powder obtained by mechanical milling and surface treatment of a powder mixture of copper powder and tin powder on a ball mill (average particle size 21 µm, Sn 0.69%). Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 24 hours. The run was repeated 2 times. Reported in Table 1 are the concentrations of impurities in the metallic silicon used, an average of silane formation rate from the start to the end of reaction, and an average of cumulative content of useful silane.

Example 2

A fluidized bed reactor of carbon steel having a diameter of 75 mm and a height of 900 mm was charged with 100 parts of metallic silicon powder, a catalyst mixture of 5 parts copper oxide powder, 0.2 part zinc and 0.1 part tin, and 0.5 part of a catalyst powder obtained by mechanical milling and surface treatment of a powder mixture of copper powder and tin powder on a ball mill (average particle size 21 µm, Sn 0.69%). Then a gas mixture of methyl chloride and nitrogen was fed to the reactor at a flow rate of 14.4 Nl/min and the reactor was heated to an internal temperature of 320° C. whereupon reaction continued. The metallic silicon powder and the catalyst mixture were fed to the reactor column from its bottom so as to keep constant the amount of reaction medium within the column. The reaction was terminated after 24 hours. The run was repeated 2 times. Reported in Table 1 are the concentrations of impurities in the metallic silicon used, an average of silane formation rate from the start to the end of reaction, and an average of cumulative content of useful silane.

Example 3

A fluidized bed reactor of carbon steel having a diameter of 75 mm and a height of 900 mm was charged with 100 parts of metallic silicon powder, a catalyst mixture of 4 parts metallic copper powder, 0.2 part zinc and 0.1 part tin, and 0.5 part of a catalyst powder obtained by mechanical milling and surface treatment of a powder mixture of copper powder and tin powder on a stamp mill (average particle size 25 µm, Sn 0.48%). Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 24 hours. The run was repeated 2 times. Reported in Table 1 are the concentrations of impurities in the metallic silicon used, an average of silane formation rate from the start to the end of reaction, and an average of cumulative content of useful silane.

Example 4

A fluidized bed reactor of carbon steel having a diameter of 75 mm and a height of 900 mm was charged with 100 parts of metallic silicon powder, a catalyst mixture of 5 parts copper oxide powder, 0.2 part zinc and 0.1 part tin, and 0.5 part of a catalyst powder obtained by mechanical milling and surface treatment of a powder mixture of copper powder and tin powder on a stamp mill (average particle size 25 μm, Sn 0.48%). Then a gas mixture of methyl chloride and nitrogen was fed to the reactor at a flow rate of 14.4 Nl/min and the reactor was heated to an internal temperature of 320° C. whereupon reaction continued. The metallic silicon powder and the catalyst mixture were fed to the reactor column from its bottom so as to keep constant the amount of reaction medium within the column. The reaction was terminated after 24 hours. The run was repeated 2 times. Reported in Table 1 are the concentrations of impurities in the metallic silicon used, an average of silane formation rate from the start to the end of reaction, and an average of cumulative content of useful silane.

Example 5

A fluidized bed reactor of carbon steel having a diameter of 75 mm and a height of 900 mm was charged with 100 parts of metallic silicon powder, a catalyst mixture of 4 parts metallic copper powder, 0.2 part zinc and 0.1 part tin, and 0.5 part of a catalyst powder obtained by mechanical milling and surface treatment of a powder mixture of copper powder and tin powder on a jet mill (average particle size 17 μm, Sn 0.39%). Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 24 hours. The run was repeated 2 times. Reported in Table 1 are the concentrations of impurities in the metallic silicon used, an average of silane formation rate from the start to the end of reaction, and an average of cumulative content of useful silane.

Example 6

A fluidized bed reactor of carbon steel having a diameter of 75 mm and a height of 900 mm was charged with 100 parts of metallic silicon powder, a catalyst mixture of 5 parts copper oxide powder, 0.2 part zinc and 0.1 part tin, and 0.5 part of a catalyst powder obtained by mechanical milling and surface treatment of a powder mixture of copper powder and tin powder on a jet mill (average particle size 17 μm, Sn 0.39%). Then a gas mixture of methyl chloride and nitrogen was fed to the reactor at a flow rate of 14.4 Nl/min and the reactor was heated to an internal temperature of 320° C. whereupon reaction continued. The metallic silicon powder and the catalyst mixture were fed to the reactor column from its bottom so as to keep constant the amount of reaction medium within the column. The reaction was terminated after 24 hours. The run was repeated 2 times. Reported in Table 1 are the concentrations of impurities in the metallic silicon used, an average of silane formation rate from the start to the end of reaction, and an average of cumulative content of useful silane.

Example 7

A fluidized bed reactor of carbon steel having a diameter of 75 mm and a height of 900 mm was charged with 100 parts of metallic silicon powder, a catalyst mixture of 4 parts metallic copper powder, 0.2 part zinc and 0.1 part tin, and 0.5 part of a catalyst powder obtained by mechanical mixing and surface treatment of a powder mixture of copper powder and tin powder on a mechanofusion device (average particle size 29 μm, Sn 0.61%). Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 24 hours. The run was repeated 2 times. Reported in Table 1 are the concentrations of impurities in the metallic silicon used, an average of silane formation rate from the start to the end of reaction, and an average of cumulative content of useful silane.

Example 8

A fluidized bed reactor of carbon steel having a diameter of 75 mm and a height of 900 mm was charged with 100 parts of metallic silicon powder, a catalyst mixture of 5 parts copper oxide powder, 0.2 part zinc and 0.1 part tin, and 0.4 part of a catalyst powder obtained by mechanical mixing and surface treatment of a powder mixture of copper powder and tin powder on a mechanofusion device (average particle size 29 μm, Sn 0.61%). Then a gas mixture of methyl chloride and nitrogen was fed to the reactor at a flow rate of 14.4 Nl/min and the reactor was heated to an internal temperature of 320° C. whereupon reaction continued. The metallic silicon powder and the catalyst mixture were fed to the reactor column from its bottom so as to keep constant the amount of reaction medium within the column. The reaction was terminated after 24 hours. The run was repeated 2 times. Reported in Table 1 are the concentrations of impurities in the metallic silicon used, an average of silane formation rate from the start to the end of reaction, and an average of cumulative content of useful silane.

Comparative Example 1

A fluidized bed reactor of carbon steel having a diameter of 75 mm and a height of 900 mm was charged with 100 parts of metallic silicon powder and a catalyst mixture of 4 parts metallic copper powder, 0.2 part zinc and 0.1 part tin. Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 20 hours. The run was repeated 4 times. Reported in Table 1 are the concentrations of impurities in the metallic silicon used, an average of silane formation rate from the start to the end of reaction, and an average of cumulative content of useful silane.

Comparative Example 2

A fluidized bed reactor of carbon steel having a diameter of 75 mm and a height of 900 mm was charged with 100 parts of metallic silicon powder and a catalyst mixture of 5 parts copper oxide powder, 0.2 part zinc and 0.1 part tin. Then a gas mixture of methyl chloride and nitrogen was fed to the reactor at a flow rate of 14.4 Nl/min and the reactor was heated to an internal temperature of 320° C. whereupon reaction continued. The metallic silicon powder and the catalyst mixture were fed to the reactor column from its bottom so as to keep constant the amount of reaction medium within the column. The reaction was terminated after 20 hours. The run was repeated 2 times. Reported in Table 1 are the concentrations of impurities in the metallic silicon used, an average of silane formation rate from the start to the end of reaction, and an average of cumulative content of useful silane.

Comparative Example 3

A fluidized bed reactor of carbon steel having a diameter of 75 mm and a height of 900 mm was charged with 100 parts of metallic silicon powder, a catalyst mixture of 4 parts metallic copper powder, 0.2 part zinc and 0.1 part tin, and 0.5 part of a copper-tin alloy (formulation Cu 99.56%, Sn 0.44%). Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 10 hours. The run was repeated 2 times. Reported in Table 1 are the concentrations of impurities in the metallic silicon used, an average of silane formation rate from the start to the end of reaction, and an average of cumulative content of useful silane.

Comparative Example 4

A fluidized bed reactor of carbon steel having a diameter of 75 mm and a height of 900 mm was charged with 100 parts of metallic silicon powder, a catalyst mixture of 5 parts copper oxide powder, 0.2 part zinc and 0.1 part tin, and 0.5 part of a copper-tin alloy (formulation Cu 99.56%, Sn 0.44%). Then a gas mixture of methyl chloride and nitrogen was fed to the reactor at a flow rate of 14.4 Nl/min and the reactor was heated to an internal temperature of 320° C. whereupon reaction continued. The metallic silicon powder and the catalyst mixture were fed to the reactor column from its bottom so as to keep constant the amount of reaction medium within the column. The reaction was terminated after 10 hours. The run was repeated 2 times. Reported in Table 1 are the concentrations of impurities in the metallic silicon used, an average of silane formation rate from the start to the end of reaction, and an average of cumulative content of useful silane.

Example 9

A fluidized bed reactor of carbon steel having a diameter of 75 mm and a height of 900 mm was charged with 100 parts of metallic silicon powder, a catalyst mixture of 4 parts metallic copper powder, 0.2 part zinc and 0.1 part tin, and 0.5 part of a catalyst powder obtained by mechanical milling and surface treatment of a powder mixture of brass powder (Cu 80%, Zn 20%) and tin powder on a ball mill (average particle size 22 µm, Sn 0.57%). Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 24 hours. The run was repeated 2 times. Reported in Table 1 are the concentrations of impurities in the metallic silicon used, an average of silane formation rate from the start to the end of reaction, and an average of cumulative content of useful silane.

Example 10

A fluidized bed reactor of carbon steel having a diameter of 75 mm and a height of 900 mm was charged with 100 parts of metallic silicon powder, a catalyst mixture of 4 parts metallic copper powder, 0.2 part zinc and 0.1 part tin, and 0.5 part of a catalyst powder obtained by mechanical milling and surface treatment of a powder mixture of brass powder (Cu 80%, Zn 20%) and tin powder on a stamp mill (average particle size 18 µm, Sn 0.56%). Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 24 hours. The run was repeated 2 times. Reported in Table 1 are the concentrations of impurities in the metallic silicon used, an average of silane formation rate from the start to the end of reaction, and an average of cumulative content of useful silane.

Example 11

A fluidized bed reactor of carbon steel having a diameter of 75 mm and a height of 900 mm was charged with 100 parts of metallic silicon powder, a catalyst mixture of 4 parts metallic copper powder, 0.2 part zinc and 0.1 part tin, and 0.5 part of a catalyst powder obtained by mechanical mixing and surface treatment of a powder mixture of brass powder (Cu 80%, Zn 20%) and tin powder on a mechanofusion device (average particle size 33 µm, Sn 0.68%). Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 24 hours. The run was repeated 2 times. Reported in Table 1 are the concentrations of impurities in the metallic silicon used, an average of silane formation rate from the start to the end of reaction, and an average of cumulative content of useful silane.

Example 12

A fluidized bed reactor of carbon steel having a diameter of 75 mm and a height of 900 mm was charged with 100 parts of metallic silicon powder, a catalyst mixture of 5 parts metallic copper powder, 0.2 part zinc and 0.1 part tin, and 0.5 part of a catalyst powder obtained by mechanical mixing and surface treatment of a powder mixture of phosphorus-copper alloy (Cu 92%, P 8%) and tin powder on a ball mill (average particle size 23 µm, Sn 0.43%). Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 24 hours. The run was repeated 2 times. Reported in Table 1 are the concentrations of impurities in the metallic silicon used, an average of silane formation rate from the start to the end of reaction, and an average of cumulative content of useful silane.

Example 13

A fluidized bed reactor of carbon steel having a diameter of 75 mm and a height of 900 mm was charged with 100 parts of metallic silicon powder, a catalyst mixture of 4 parts metallic copper powder, 0.2 part zinc and 0.1 part tin, and 0.5 part of a catalyst powder obtained by mechanical mixing and surface treatment of a powder mixture of phosphorus-copper alloy (Cu 92%, P 8%) and tin powder on a stamp mill (average particle size 30 µm, Sn 0.62%). Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 24 hours. The run was repeated 2 times. Reported in Table 1 are the concentrations of impurities in the metallic silicon used, an average of silane formation rate from the start to the end of reaction, and an average of cumulative content of useful silane.

Example 14

A fluidized bed reactor of carbon steel having a diameter of 75 mm and a height of 900 mm was charged with 100 parts of metallic silicon powder, a catalyst mixture of 5 parts copper oxide powder, 0.2 part zinc and 0.1 part tin, and 0.5 part of a catalyst powder obtained by mechanical mixing and surface treatment of a powder mixture of phosphorus-copper alloy (Cu 85%, P 15%) and tin powder on a mechanofusion device (average particle size 36 µm, Sn 0.58%). Then a gas mixture of methyl chloride and nitrogen was fed to the reactor at a flow rate of 14.4 Nl/min and the reactor was heated to an internal temperature of 320° C. whereupon reaction continued. The metallic silicon powder and the catalyst mixture were fed to the reactor column from its bottom so as to keep constant the amount of reaction medium within the column. The reaction was terminated after 24 hours. The run was repeated 2 times. Reported in Table 1 are the concentrations of impurities in the metallic silicon used, an average of silane formation rate from the start to the end of reaction, and an average of cumulative content of useful silane.

TABLE 1

| | Reaction temp. (° C.) | Fe (%) | Al (%) | Ca (%) | Catalyst powder added | | | | Bulk specific gravity (g/cm$^3$) | Silane formation rate (g/h)[b] | Useful silane content (%)[c] |
| --- | --- | --- | --- | --- | --- | --- | --- | --- | --- | --- | --- |
| | | | | | Addition | Surface treatment | Sn concentration (%) | Additive concentration (%/Si)[a] | | | |
| Example 1 | 310 | 0.25 | 0.18 | 0.06 | yes | ball mill | 0.69 | 0.50 | 0.78 | 572 | 89.2 |
| Example 2 | 320 | 0.27 | 0.14 | 0.07 | yes | ball mill | 0.69 | 0.50 | 0.78 | 494 | 87.8 |
| Example 3 | 310 | 0.27 | 0.17 | 0.06 | yes | stamp mill | 0.48 | 0.50 | 0.71 | 616 | 89.5 |
| Example 4 | 320 | 0.26 | 0.16 | 0.07 | yes | stamp mill | 0.48 | 0.50 | 0.71 | 551 | 88.6 |
| Example 5 | 310 | 0.27 | 0.18 | 0.07 | yes | jet mill | 0.39 | 0.50 | 0.65 | 565 | 88.8 |
| Example 6 | 320 | 0.27 | 0.16 | 0.07 | yes | jet mill | 0.39 | 0.50 | 0.65 | 507 | 90.1 |
| Example 7 | 310 | 0.26 | 0.18 | 0.06 | yes | mechanofusion | 0.61 | 0.50 | 0.83 | 654 | 88.4 |
| Example 8 | 320 | 0.28 | 0.15 | 0.08 | yes | mechanofusion | 0.61 | 0.50 | 0.83 | 530 | 89.0 |
| Comparative Example 1 | 310 | 0.25 | 0.14 | 0.06 | no | — | — | — | 1.06 | 289 | 87.7 |
| Comparative Example 2 | 320 | 0.27 | 0.15 | 0.07 | no | — | — | — | 1.06 | 267 | 85.1 |
| Comparative Example 3 | 310 | 0.28 | 0.13 | 0.08 | yes | — | 0.44 | 0.50 | 0.89 | 293 | 79.3 |
| Comparative Example 4 | 320 | 0.27 | 0.12 | 0.06 | yes | — | 0.44 | 0.50 | 0.89 | 288 | 77.5 |
| Example 9 | 310 | 0.28 | 0.16 | 0.07 | yes | ball mill | 0.57 | 0.50 | 1.20 | 415 | 88.0 |
| Example 10 | 310 | 0.25 | 0.16 | 0.07 | yes | stamp mill | 0.56 | 0.50 | 1.17 | 439 | 89.8 |
| Example 11 | 310 | 0.26 | 0.17 | 0.08 | yes | mechanofusion | 0.68 | 0.50 | 1.04 | 523 | 87.9 |
| Example 12 | 310 | 0.27 | 0.14 | 0.06 | yes | ball mill | 0.43 | 0.50 | 1.92 | 509 | 89.4 |
| Example 13 | 310 | 0.28 | 0.17 | 0.07 | yes | stamp mill | 0.62 | 0.50 | 1.41 | 642 | 90.3 |
| Example 14 | 320 | 0.25 | 0.16 | 0.07 | yes | mechanofusion | 0.58 | 0.50 | 1.48 | 701 | 89.2 |

[a]Concentration of additive (catalyst powder) relative to silicon

[b,c]an average of four runs for Comparative Example 1 and an average of two runs for Comparative Examples 2-4 and Examples 1-14

Japanese Patent Application No. 2004-077709 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A process for preparing organohalosilanes having the general formula (I):

$$R_k(H)_mSiX_{(4-k-m)}$$

wherein R is a monovalent hydrocarbon group of 1 to 12 carbon atoms, X is a halogen atom, k is an integer of 1 to 3, m is an integer of 0 to 2, and the sum of k+m is 1 to 3, by reacting metallic silicon particles with an organohalide in the presence of a copper-containing catalyst,
  wherein a contact mass comprising the metallic silicon and a copper-containing catalyst component contains an effective amount of a catalyst powder obtained by mechanical surface treatment of a powder mixture consisting essentially of metallic powder, said metallic powder containing metallic tin powder and at least one metallic powder selected from the group consisting of copper powder, brass powder and bronze powder so as to attach the tin powder to the surface of the metal powder,
  wherein said catalyst powder contains 0.001 to 1% by weight of tin; and
  wherein said catalyst powder has a bulk specific gravity of 0.3 to 5 g/cm³ and an average particle size of 1 to 200 μm as measured by laser diffraction particle size distribution analysis.

2. The process of claim 1, wherein the mechanical surface treatment uses a mechanical grinding or mixing device selected from the group consisting of a ball mill, stamp mill, vertical roller mill, mechanofusion device, jet mill, attritor, and cosmo-phoresis mixer.

3. The process of claim 1, wherein said catalyst component comprises metallic copper or a copper compound and optionally a co-catalyst selected from the group consisting of metallic zinc, zinc compounds, metallic tin, tin compounds, metallic antimony, antimony compounds, metallic aluminum, aluminum compounds, metallic phosphorus and phosphorus compounds.

4. The process of claim 1, wherein the catalyst powder has an average particle size of 1 to 200 μm as measured by laser diffraction particle size distribution analysis.

5. The process of claim 1, wherein the organohalide is that of formula (II):

$$RX \qquad (II)$$

wherein R is a monovalent hydrocarbon group of 1 to 12 carbon atoms and X is a halogen atom.

6. The process claim 5, wherein R is a monovalent hydrocarbon group of 1 to 16 carbon atoms.

7. The process of claim 5, wherein X is chlorine.

8. The process of claim 5, wherein X is bromine.

9. The process of claim 1, wherein the organohalide is a member selected from the group consisting of methyl chloride, ethyl chloride, propyl chloride, methyl bromide, ethyl bromide, benzene chloride and benzene bromide.

10. The process of claim 1, wherein the reacting is effected at a temperature of about 250 to 600° C.

11. The process of claim 1, wherein the reacting is effected at a temperature of about 350 to 500° C.

12. A process for preparing organohalosilanes having the general formula (I):

$$R_k(H)_mSiX_{(4-k-m)}$$

wherein R is a monovalent hydrocarbon group of 1 to 12 carbon atoms, X is a halogen atom, k is an integer of 1 to 3 in is an integer of 0 to 2, and the sum of k+m is 1 to 3, which comprises the steps of:
  obtaining a catalyst powder obtained by mechanical surface treatment of a powder mixture consisting essentially of metallic powder, said metallic powder containing metallic tin powder and at least one metallic powder selected from the group consisting of copper powder, brass powder and bronze powder so as to attach the tin powder to the surface of the metal powder; and
  obtaining a contact mass comprising a metallic silicon, a copper-containing catalyst component and an effective amount of the catalyst powder,
  reacting the metallic silicon particles in the contact mass with an organohalide in the presence of the copper-containing catalyst and the catalyst powder,
  wherein said catalyst powder contains 0.001 to 1% by weight of tin; and
  wherein said catalyst powder has a bulk specific gravity of 0.3 to 5 g/cm³ and an average particle size of 1 to 200 μm as measured by laser diffraction particle size distribution analysis.

13. The process of claim 12, wherein the mechanical surface treatment uses a mechanical grinding or mixing device selected from the group consisting of a ball mill, stamp mill, vertical roller mill, mechanofusion device, jet mill, attritor, and cosmo-phoresis mixer.

14. The process of claim 12, wherein said catalyst component comprises metallic copper or a copper compound and optionally a co-catalyst selected from the group consisting of metallic zinc, zinc compounds, metallic tin, tin compounds, metallic antimony, antimony compounds, metallic aluminum, aluminum compounds, metallic phosphorus and phosphorus compounds.

15. Process of claim 12, wherein the catalyst powder has an average particle size of 1 to 200 μm as measured by laser diffraction particle size distribution analysis.

16. The process of claim 12, wherein the organohalide is that of formula (II):

$$RX \qquad (II)$$

wherein R is a monovalent hydrocarbon group of 1 to 12 carbon atoms and X is a halogen atom.

17. The process of claim 16, wherein R is a monovalent hydrocarbon group of 1 to 16 carbon atoms.

18. The process of claim 16, wherein X is chlorine.

19. The process of claim 16, wherein X is bromine.

20. The process of claim 12, wherein the organohalide is a member selected from the group consisting of methyl chloride, ethyl chloride, propyl chloride, methyl bromide, ethyl bromide, benzene chloride and benzene bromide.

21. The process of claim 12, wherein the reacting is effected at a temperature of about 250 to 600° C.

22. The process of claim 12, wherein the reacting is effected at a temperature of about 350 to 500° C.

* * * * *